United States Patent [19]

Albanese et al.

[11] Patent Number: 5,684,181

[45] Date of Patent: Nov. 4, 1997

[54] PROCESS FOR THE PREPARATION OF SULFONATED ARYLPHOSPHINES

[75] Inventors: Guido Albanese, München; Rainer Manetsberger, Wielenbach; Wolfgang A. Herrmann, Gartenstrasse; Christine Schwer, München, all of Germany

[73] Assignee: Hoechst Aktiengesellschaft, Germany

[21] Appl. No.: 537,357

[22] Filed: Oct. 2, 1995

[30] Foreign Application Priority Data

Sep. 30, 1994 [DE] Germany ............................ 44 35 190.9

[51] Int. Cl.$^6$ ............................................................ C07F 9/50
[52] U.S. Cl. ................................................ 562/35; 568/13
[58] Field of Search ............................ 562/35; 568/13

[56] References Cited

U.S. PATENT DOCUMENTS

| | | | |
|---|---|---|---|
| 4,483,802 | 11/1984 | Gärtner et al. | 260/505 C |
| 4,668,824 | 5/1987 | Jenck et al. | 568/15 |
| 5,274,183 | 12/1993 | Herrmann et al. | 562/35 |
| 5,451,698 | 9/1995 | Bahrmann et al. | 562/35 |

*Primary Examiner*—C. Warren Ivy
*Assistant Examiner*—Jean F. Vollano
*Attorney, Agent, or Firm*—Bierman, Muserlian and Lucas, LLP

[57] ABSTRACT

The sulfonation of arylphosphines, which contain at least one aromatic radical which can be sulfonated, is carried out with an anhydrous mixture of sulfuric acid and orthoboric acid. By choosing the appropriate reaction temperature, the process allows selective introduction of the desired number of sulfonic acid radicals into the phosphine molecule and avoids the formation of phosphine oxides. When separating the sulfonation mixture, the orthoboric acid can be separated off together with the sulfuric acid.

20 Claims, No Drawings

PROCESS FOR THE PREPARATION OF SULFONATED ARYLPHOSPHINES

This Application claims the priority of German Application P 44 35 190.9, filed Sep. 30, 1994.

The Invention is directed to a process for the preparation of sulfonated arylphosphines by reaction of arylphosphines with an anhydrous mixture of sulfuric acid and orthoboric acid. The novel process avoids side reactions, in particular the formation of phosphine oxides.

BACKGROUND OF THE INVENTION

Complex compounds which contain, as the central atom, a metal of Group VIII A of the Periodic Table (IUPAC version) and, as ligands, P(III) compounds, such as phosphines, and optionally additional groups capable of complex formation, have gained increasing importance as catalysts in recent years. The reaction of olefins with synthesis gas to give aldehydes (hydroformylation), which is used industrially on a large scale, is carried out in the presence of catalysts which comprise cobalt (and in particular, rhodium) and triphenylphosphine. In accordance with the solubility of these catalysts in organic media, the reaction proceeds in a homogeneous phase.

Alternatively, this reaction can also be carried out in a heterogeneous reaction system, like other catalytic reactions. This independent development is not limited to complex compounds of metals of Group VIII A, but also includes complex compounds of Groups VII A and I B of the Periodic Table (IUPAC version). Catalysts dissolved in water have the advantage of being easily and gently separated from the reaction product which is insoluble in water. The process described in DE-C-27 00 904 for addition of hydrogen cyanide to an unsaturated organic compound having at least one ethylenic double bond, for example, operates in accordance with this principle. Suitable catalysts for this reaction are nickel/TPPTS [TPPTS means tris(m-sulfonato-phenyl) phosphine], palladium/TPPTS, or iron/TPPTS. For the preparation of aldehydes by reaction of olefins with carbon monoxide and hydrogen, rhodium in metallic form or as one of its compounds, together with a water-soluble phosphine—for example TPPTS—is employed as the catalyst in accordance with the process of DE-C-26 27 354. EP-A-372 313, for example, relates to other catalysts of the type mentioned and their use in various reactions, such as hydrogenation, allene-alkyne coupling, and amine addition to double bonds.

Sulfonated phenylphosphines are obtained by the process described in J. Chem. Soc., 1958, pages 281, 282 by reaction of triphenylphosphine with oleum, heating of the reaction mixture on a waterbath, dilution of the reaction product with water, and neutralization with sodium hydroxide. The sodium salt of diphenyl(m-sulfonatophenyl)phosphine crystallizes out of the sulfonation mixture.

Disodium salts of di(m-sulfonatophenyl)phenylphosphine and of tri(m-sulfonatophenyl)phosphine are obtained by similar processes. The starting substance in both cases is again triphenylphosphine, which is reacted with oleum at temperatures of between 18° and 40° C. over a period of 15 to 63 hours. The reaction product is in turn diluted with water and neutralized with sodium hydroxide, and it should be ensured that temperatures below 20° C. are maintained in the mixture during the addition of the sodium hydroxide (DE-C-26 27 354). In addition, to monophosphines, sulfonated di- and polyphosphines are also used as substituents of catalysts. Examples of their preparation are to be found in DE-A-40 40 314.

A disadvantage of all the known processes for obtaining sulfonated arylphosphines is the unwanted formation of phosphorus-oxygen compounds, i.e. the oxidation of trivalent phosphorus by sulfur trioxide or molecular oxygen to give pentavalent phosphorus. The resulting phosphine oxides are not capable of forming catalytically active complex bonds with metal ions; therefore, they are of no value as catalyst components. They are usually separated selectively from the sulfonation product mixture so that the catalyst solution is not loaded excessively by inert substances. To limit the oxidation, the reaction is carried out at the lowest possible sulfonation temperatures. This measure leads to the formation of water-soluble phosphines, in which the maximum possible degree of sulfonation,—the highest solubility which can be achieved in water (which is important for retention of the metal component of the catalyst system in water) is not achieved. A more extensive sulfonation by prolonging the reaction time is contraindicated by the resulting increased oxidation.

SUMMARY OF THE INVENTION

It is, therefore, an object of the Invention to develop a process which avoids the oxidation of the phosphines which accompanies sulfonation, thereby allowing higher reaction temperatures, longer reaction times, and better control of the reaction to establish a defined degree of sulfonation within wide limits.

The Invention is directed to a process for the preparation of sulfonated arylphosphines by sulfonation of mono-, di-, oligo- or polyphosphines containing aryl groups. It comprises sulfonation at temperatures between 20° and 350° C. with an anhydrous mixture of sulfuric acid and orthoboric acid.

Surprisingly, it has been found that the use of an anhydrous mixture of sulfuric acid and orthoboric acid as the sulfonating agent considerably reduces—or suppresses entirely—the formation of phosphine oxides, even with phosphines which are particularly sensitive to oxidation. The reaction can therefore be carried out at a higher temperature and/or over a longer period of time than with the sulfonating agent oleum used to date. Furthermore, by choosing the reaction temperature, it is possible to carry out the sulfonation selectively, i.e. to influence the degree of sulfonation. Separation of the sulfonation mixture is also simplified, inter alia because of the lower evolution of heat during the hydrolysis.

An essential feature of the procedure according to the Invention is the use of an anhydrous mixture of the two components as the sulfonating agent. The sulfuric acid is therefore expediently employed in the anhydrous form. Furthermore, it is necessary that the water formed in the sulfonating reagent $H_2SO_4/H_3BO_3$ in accordance with the equation

$$5\, H_2SO_4 + B(OH)_3 \rightleftharpoons H_3SO_4^+ + 3\, H_2O + B(OSO_3H)_4^-$$

be removed from the reaction mixture by water binding substances. Sulfur trioxide which forms, with water, sulfuric acid (a compound native to the reaction) has proven particularly suitable for this purpose. It is expediently employed in the form of oleum. The water-binding reagent is metered into the reaction mixture at the rate at which water is formed.

Another constituent of the sulfonation mixture is orthoboric acid. This is used in commercially available form; particular purification is not necessary. The acid is employed in approximately equimolar amounts, based on the P(III) atoms contained in the phosphine to be sulfonated, so that one mole of boric acid is present per mole of phosphorus. Less than the equimolar amount does no harm, but an excess is preferred. It is particularly advantageous to dissolve the orthoboric acid in the sulfuric acid until saturation is reached.

DETAILED DESCRIPTION OF THE INVENTION

Starting compounds for the sulfonation are arylphosphines. This general term is understood to include mono-, di-, oligo-, and polyphosphines which contain at least one sulfonatable aromatic radical. The aromatic radical can consist of one or more benzene rings which are bonded by a single C—C bond, like biphenyl, or in which the carbon rings have two or more common carbon atoms (condensed ring systems), like naphthyl. The aromatic radicals can themselves be mono- or poly-substituted, for example by chlorine, fluorine, and/or alkyl, alkoxy, and/or nitro groups. Examples of such monophosphines are dimethylphenyl-, methyldiphenyl- and triphenylphosphines. The group of diphosphines is exemplified by 2,2'-bis(diphenylphosphinomethyl)biphenyl and 2,2'-bis(diphenylphosphinomethyl)-1,1'-binaphthyl. Phosphines are also understood as comprising compounds of trivalent phosphorus in which the phosphorus atom is a constituent of a ring system. Examples of these compounds are phosphorobenzene substituted by aromatic radicals, and aryl- and/or alkyl-substituted phospholes and phosphanorbornadienes.

Arylphosphines in commercially available form or in the form obtained during synthesis are amenable to sulfonation by the process according to the Invention. Special purification is not necessary, unless the subsequent use of the sulfonated compounds—for example as catalyst constituents—require this.

It is expedient to add the boric acid to the sulfuric acid even before introduction of the phosphine and to bind the water formed. The addition of the phosphine to the sulfonation reagent is carried out portionwise at 20° to 120° C.; rapid and uniform distribution and dissolution of the phosphorus compound in the reaction mixture being ensured, for example, by stirring. It has proven appropriate to add the phosphorus compound in dissolved form to the sulfonation reagent. Anhydrous sulfuric acid is preferably used as the solvent. Complete solution of the phosphine in the H$_2$SO$_4$/H$_3$BO$_3$ mixture ensures that sulfuric acid is present in excess. The sulfonation is carried out at temperatures of 20° to 350° C. The actual reaction temperature depends on the nature of the phosphine and the degree of sulfonation, and must be determined beforehand, if appropriate, by orienting experiments. The basic rule is that, as the temperature increases, the degree of sulfonation increases. The pronounced dependence of the degree of sulfonation on temperature allows a predetermined number of sulfonic acid groups to be introduced selectively into the phosphine molecule. Thus, for example, triphenylphosphine is monosulfonated at 20° C. and disulfonated at 60° C. In order to maintain the temperature as uniform as possible, it is advisable to stir the reaction mixture. The reaction time depends on the nature of the phosphine and on the number of sulfonic acid groups which are to be introduced into the phosphine molecule. In general, it is several hours to several days.

When the reaction has ended, the reaction mixture is diluted with water and the end product recovered. In a preferred process, the resulting acidic aqueous solution of the sulfonation product is extracted with a solution of a water-insoluble amine in a water-insoluble organic solvent. Sulfonated arylphosphines, which are largely free from the Lewis acids added in the sulfonation step, are obtained by this route. This procedure is particularly suitable if boric acid is used as the Lewis acid.

Specifically, with this method, water, preferably oxygen-free, is added to the sulfonation mixture in an amount necessary for dilution of the sulfuric acid present to 0.5% to 50% by weight, preferably 25% to 35% by weight. The water-insoluble amine, dissolved in a water-insoluble organic solvent, is added to the diluted solution. The concentration of the amine in the solution is 1.0% to 35% by weight, preferably 10% to 30% by weight and, in particular, 13% to 25% by weight.

0.5 to 3.0 mol, preferably 0.5 to 2.5 mol, of amine are used per chemical equivalent of sulfonic acid. The use of excess amine ensures that only low phosphine losses occur. A higher excess of amine than that stated above is indeed possible, but does not lead to improvement in the separation, purification, or yield.

After intensive mixing, two phases are formed. The aqueous phase of higher specific gravity contains the sulfuric acid and virtually all the orthoboric acid, and the low-sulfate organic phase, which is substantially free from orthoboric acid, contains the amine salt of the sulfonated phosphine dissolved therein. The two phases are separated from each other. If appropriate, the organic phase is washed, for example, with water, to remove any residual dissolved boric acid, and is then reacted with an aqueous solution of an inorganic base. The base is employed here in an amount equivalent to the amount of dissolved amine salt. Excess base is to be avoided because it contaminates the end product. The aqueous solution of the sulfonated arylphosphine is obtained in this manner; the water-insoluble amine is recovered and is available for renewed use.

The process described can be carried out either batchwise or continuously. Apparatuses customary for separation of substances, such as countercurrent extraction units, are used. Instead of adding the base dissolved in water to the solution of the amine salt in the organic medium all at once, in a preferred embodiment, the addition can be carried out in portions. This procedure is employed with success particularly for the separation of a sulfonation mixture which contains the products of various sulfonation stages.

Insoluble amines suitable for the process are water-insoluble homo- and heterocyclic, aliphatic, aromatic, araliphatic, and (preferably open-chain) branched or unbranched aliphatic amines having 10 to 60, preferably 13 to 36, carbon atoms. Amines, the salts of which with the sulfonic acids are insoluble or have only a limited solubility in the organic solvent, are less suitable. Particularly appropriate amines are tri-n-octylamine, triisooctylamine, tri-2-ethylhexylamine, and tridodecylamine.

The amines are dissolved in a water-insoluble organic solvent. Aliphatic or aromatic hydrocarbons or hydrocarbon mixtures, for example, toluene or kerosine, as well as alcohols having 4 to 20 carbon atoms and ethers having 8 to 20 carbon atoms are particularly suitable. Suitable bases for transfer of the phosphines in sulfonic acid into the aqueous phase are the hydroxides of the alkali metals and alkaline earth metals, in particular alkali metal hydroxides, ammonia, and the alkali metal carbonates.

The separation is expediently carried out at 0° to 40° C., preferably from room temperature to about 40° C. Higher temperatures provide no advantages. The information on the solubility of the amines and of the organic solvents in water relates here in each case to the temperatures at which the process is carried out. The end product is either left in the aqueous solution or may be obtained in solid form by evaporation, crystallization, decanting, or filtration.

The novel process is illustrated in the following examples, but is not limited thereto.

EXAMPLE 1

Preparation of Di(m-sulfonatophenyl) phenylphosphine 20 ml of oleum (65% by weight $SO_3$) is added dropwise to a solution of 4.8 g (77.8 mmol) of orthoboric acid in 20 ml of concentrated sulfuric acid such that an $SO_3$ concentration of about 0.9% by weight is achieved. The excess $SO_3$ is removed at 60° C. under a high vacuum in the course of 45 minutes. 3.0 g (11.4 mmol) of triphenylphosphine is dissolved in the anhydrous $H_2SO_4/H_3BO_3$ mixture, while stirring. The reaction mixture is heated and maintained at 58° C. for 4 days and, after cooling, is hydrolyzed with 50 ml of oxygen-free water. The aqueous solution is then extracted with 16 ml of triisooctylamine in 49 ml of toluene. The organic phase is washed three times with 20 ml of water in order to separate off the boric acid completely and is then reextracted with 7.5M sodium hydroxide solution until a pH of 11.8 is established. Thereafter, the aqueous alkaline solution is neutralized with 3M sulfuric acid and evaporated to dryness in vacuo, the solid which remains is extracted with 40 ml of methanol. The disulfonated triphenylphosphine is obtained from the methanol solution as a white, vitreous solid by removal of the solvent. The yield is 4.69 g, corresponding to 94% of theoretical.

Characterization of the Product $^{31}P-\{^{1}H\}$-NMR ($D_2O$): δ=−3.38 ppm (s), (TPPDS analytical grade: δ=−3.41 ppm (s)) P/S ratio: 1:2 (according to elemental analysis, free from sodium sulfate).

EXAMPLE 2

Preparation of Pentasulfonated 2,2'-bis (diphenylphosphinomethyl)-1,1'-binaphthalene 18 ml of oleum (65% by weight $SO_3$) is added dropwise to a solution of 4.8 g (77.8 mmol) of orthoboric acid in 20 ml of concentrated sulfuric acid such that an $SO_3$ concentration of about 4.99% by weight is achieved. The excess $SO_3$ is removed at 60° C. under a high vacuum in the course of 45 minutes. 2.0 g (3.07 mmol) of 2,2'-bis (diphenylphosphinomethyl)-1,1'-binaphthalene is dissolved in the mixture, while stirring, and the mixture is heated to and maintained at 62° for 24 hours. Thereafter, the mixture is cooled to room temperature, hydrolyzed with 40 ml of oxygen-free water, and extracted with 6 ml of triisooctylamine in 40 ml of toluene. The organic phase is washed three times with 20 ml of water each time in order to separate the boric acid completely and is then reextracted with 7.5M NaOH until a pH of 11.8 is reached. Thereafter, the aqueous, alkaline solution is neutralized with 3M sulfuric acid and evaporated to dryness in vacuo; the solid which remains is extracted with 40 ml of methanol. The product is obtained as a yellow-brown, vitreous solid from the extract by removal of the solvent. The yield is 3.78 g. corresponding to 82% of theoretical.

Characterization by Analysis

The quantitative analysis of the product corresponds to the formula $C_{46}H_{41}P_2O_{20}Na_5S_5$, i.e. the sodium salt, containing five molecules of water, of pentasulfonated 2,2'-bis (diphenylphosphinomethyl)-1,1'-binaphthalene. The contents of reaction products of different degrees of sulfonation are determined by capillary electrophoresis; the analysis yielded the following results:

| Degree of sulfonation | 2-fold | 3-fold | 4-fold | 5-fold | 6-fold |
|---|---|---|---|---|---|
| Content in the reaction product (in mol%) | 0.35 | — | 17.15 | 71.3 | 11.2 |

While only a limited number of specific embodiments of the present Invention have been expressly disclosed, it is, nonetheless, to be broadly construed and not to be limited except by the character of the claims appended hereto.

What we claim is:

1. A process for the preparation of a sulfonated arylphosphine comprising sulfonation of a compound selected from the group consisting of monophosphines, diphosphines, oligophosphines and polyphosphines, said compound containing at least one aryl group, in the presence of an anhydrous mixture of sulfuric acid and orthoboric acid formed by reacting the sulfuric acid and orthoboric acid in the presence of oleum to remove the water of reaction followed by removal of excess $SO_3$ at a sulfonation temperature of 20° to 350° C. to form a reaction product wherein at least 6.8 moles of orthoboric acid are present per mole of phosphine (III).

2. The process of claim 1 wherein said sulfonation temperature is 20° to 170° C.

3. The process of claim 1 wherein said mixture comprises a water-binding agent.

4. The process of claim 3 wherein said water-binding agent is sulfur trioxide.

5. The process of claim 3 wherein said water-binding agent is oleum.

6. The process of claim 1 wherein said sulfonation is effected by introduction of a solution of said compound in anhydrous sulfuric acid into said anhydrous mixture.

7. The process of claim 1 wherein said mixture is saturated with said orthoboric acid.

8. The process of claim 1 comprising dilution of said reaction product with water to form a first aqueous solution, extraction of said first aqueous solution with an amine solution of water-insoluble amine dissolved in a water-insoluble organic solvent, whereby a first aqueous phase and a first organic phase are formed, separation of said first organic phase from said aqueous phase addition of a second aqueous solution of a base to said organic phase, whereby a second aqueous phase and a second organic phase are formed, separation of said second aqueous phase and isolation of the sulfonated arylphosphine thereof.

9. The process of claim 8 wherein 0.5 to 3 mol of said amine per chemical equivalent of sulfonic acid is employed.

10. The process of claim 8 wherein said water is added to said reaction product in a dilution amount such that said sulfuric acid is present in an acid amount of 0.5% to 50% by weight, based on said reaction product.

11. The process of claim 10 wherein said acid amount is 25% to 35% by weight.

12. The process of claim 9 wherein 0.5 to 2.5 mol of said amine per chemical equivalent of said sulfonic acid is used.

13. The process of claim 8 wherein said amine solution contains 1.0% to 35% by weight of said amine.

14. The process of claim 13 wherein said amine solution contains 10% to 30% by weight of said amine.

15. The process of claim 14 wherein said amine solution contains 13% to 25% by weight of said amine.

16. The process of claim 8 wherein said amine is an open chain, branched or unbranched, aliphatic amine having 10 to 60 carbon atoms.

17. The process of claim 16 wherein said amine has 13 to 36 carbon atoms.

18. The process of claim 8 wherein said water-insoluble amine is selected from the group consisting of tri-n-octylamine, tri-2-ethylhexylamine, and tridodecylamine.

19. The process of claim 8 wherein said water-insoluble organic solvent is selected from the group consisting of aliphatic hydrocarbons, aromatic hydrocarbons, and mixtures thereof.

20. The process of claim 19 wherein said water-insoluble organic solvent is toluene or kerosine.

* * * * *